United States Patent [19]
Brill

[11] Patent Number: 5,395,333
[45] Date of Patent: Mar. 7, 1995

[54] MULTI-LOBED SUPPORT BALLOON CATHETER WITH PERFUSION

[75] Inventor: Alan N. Brill, Minneapolis, Minn.
[73] Assignee: SciMed Life Systems, Inc., Maple Grove, Minn.
[21] Appl. No.: 115,883
[22] Filed: Sep. 1, 1993
[51] Int. Cl.⁶ ............................................. A61M 29/00
[52] U.S. Cl. ................................. 604/101; 604/96; 604/98; 606/194
[58] Field of Search ............... 604/96, 97, 98, 101, 604/104; 606/191, 192, 194, 198

[56] References Cited

U.S. PATENT DOCUMENTS

| | | |
|---|---|---|
| 3,726,273 | 4/1973 | Cole . |
| 3,834,394 | 9/1974 | Hunter . |
| 4,066,070 | 1/1978 | Utsugi ........................ 604/95 |
| 4,183,102 | 1/1980 | Guiset . |
| 4,224,929 | 9/1980 | Furihata . |
| 4,423,725 | 1/1984 | Baran et al. . |
| 4,573,966 | 3/1986 | Weikl et al. . |
| 4,581,017 | 4/1986 | Sahota . |
| 4,744,366 | 5/1988 | Jang . |
| 4,762,130 | 8/1988 | Fogarty et al. ............... 606/194 |
| 4,763,654 | 8/1988 | Jang . |
| 4,787,388 | 11/1988 | Hofmann . |
| 4,934,786 | 6/1990 | Krauter ........................ 604/95 |
| 4,944,745 | 7/1990 | Sogard . |
| 4,958,634 | 9/1990 | Jang . |
| 4,983,167 | 1/1991 | Sahota . |
| 4,990,139 | 2/1991 | Jang . |
| 5,000,734 | 3/1991 | Boussignac et al. . |
| 5,002,531 | 3/1991 | Bonzel . |
| 5,019,042 | 5/1991 | Sahota . |
| 5,071,406 | 12/1991 | Jang . |
| 5,090,958 | 2/1992 | Sahota . |
| 5,108,370 | 4/1992 | Walinsky . |
| 5,129,883 | 7/1992 | Black . |
| 5,135,484 | 8/1992 | Wright . |
| 5,147,377 | 9/1992 | Sahota . |
| 5,152,277 | 10/1992 | Honda et al. . |
| 5,160,321 | 11/1992 | Sahota . |
| 5,167,628 | 12/1992 | Boyles ........................ 604/53 |
| 5,179,961 | 1/1993 | Littleford et al. ............ 128/772 |
| 5,226,888 | 7/1993 | Arney ........................ 604/53 |
| 5,308,356 | 5/1994 | Blackshear, Jr. et al. ........ 606/194 |

FOREIGN PATENT DOCUMENTS 2659238 9/1977 Germany .................. 604/95

Primary Examiner—Peter A. Aschenbrenner
Assistant Examiner—Perry E. Van Over
Attorney, Agent, or Firm—Nawrocki, Rooney & Sivertson

[57] ABSTRACT

A perfusion balloon catheter having a plurality of balloon lobes extending from the catheter body. Each balloon lobe defines a flow passage and includes a contact surface which is adapted to contact and support a portion of a blood vessel wall.

12 Claims, 5 Drawing Sheets

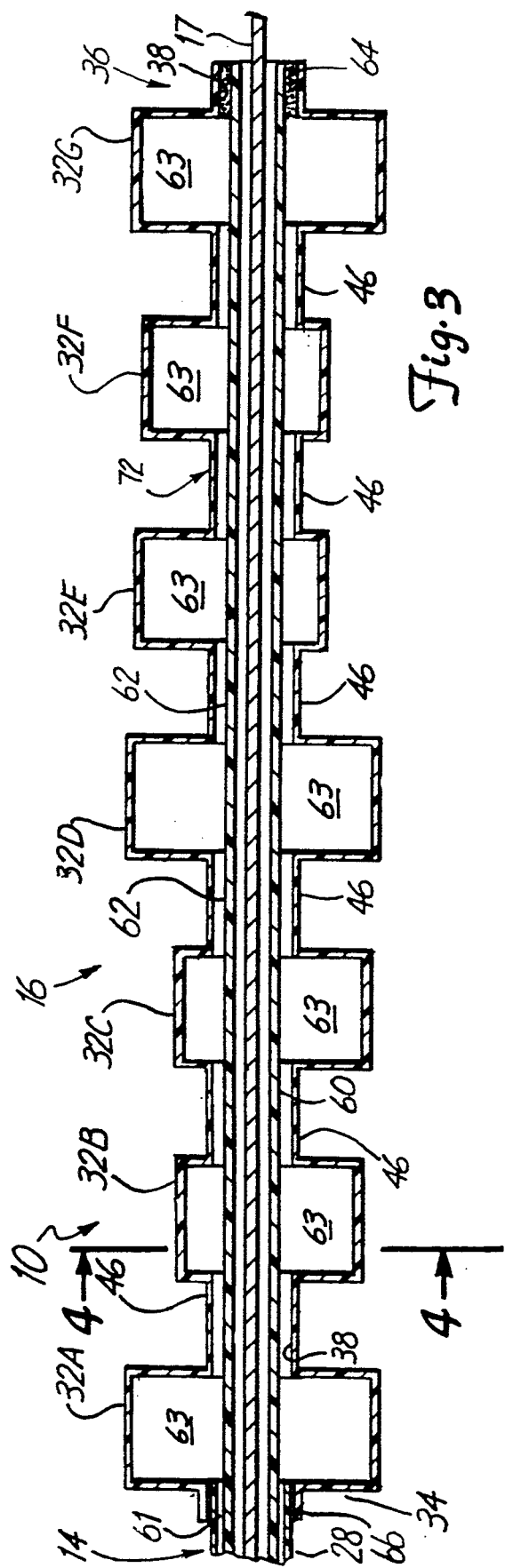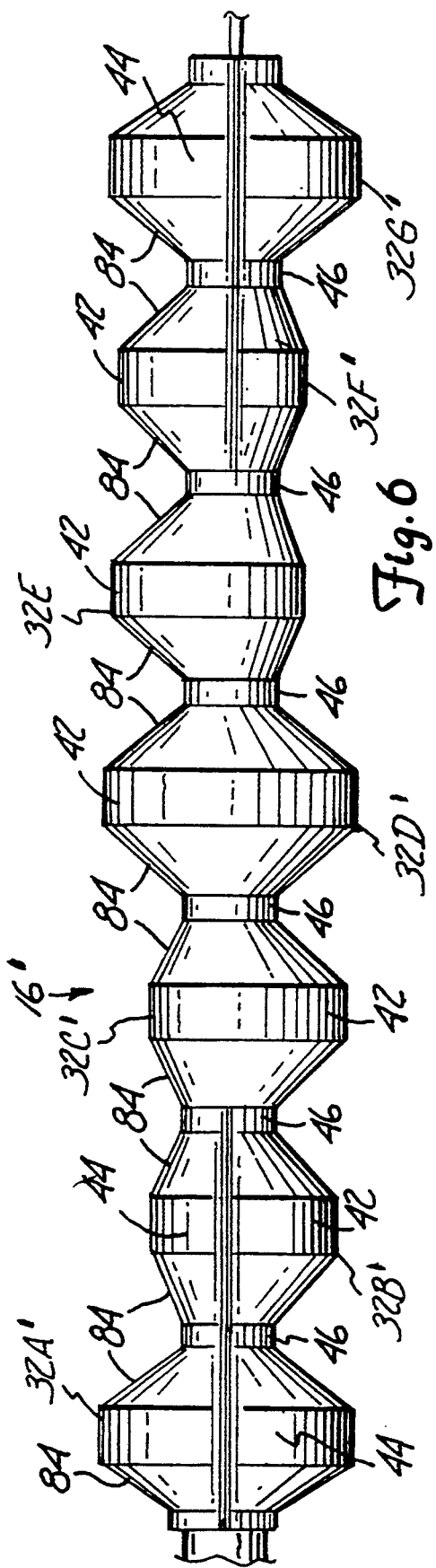

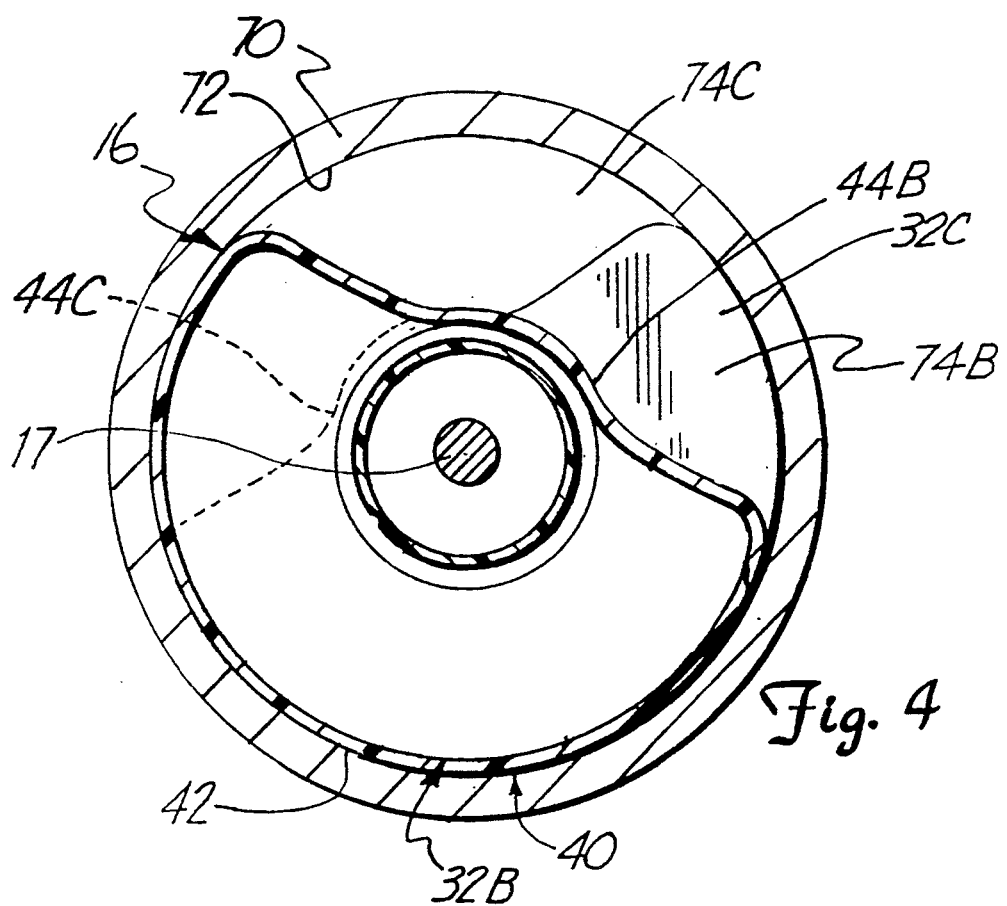

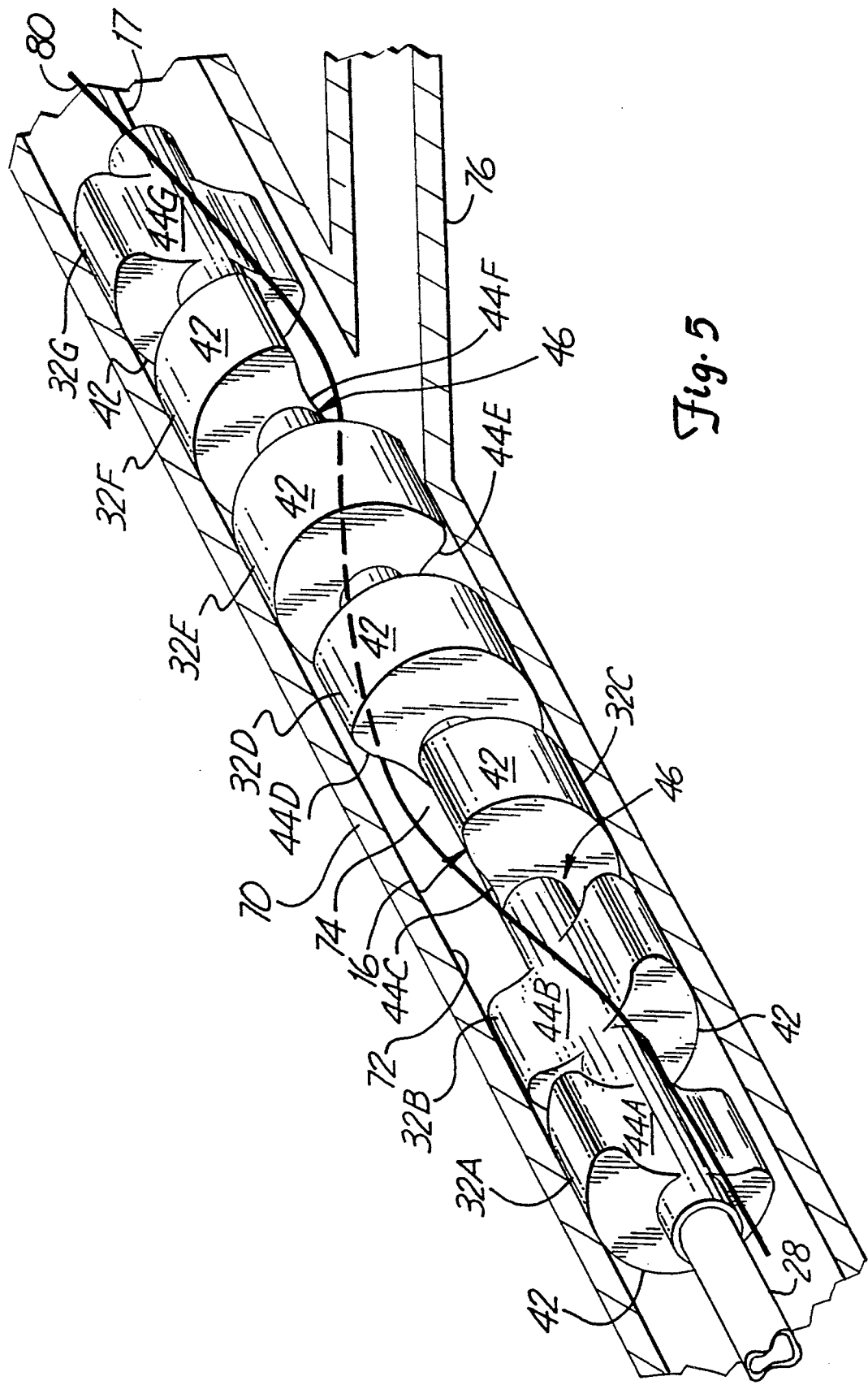

MULTI-LOBED SUPPORT BALLOON CATHETER WITH PERFUSION

BACKGROUND OF THE INVENTION

The present invention relates to balloon catheters and, particularly, to a balloon catheter having a plurality of balloon elements or lobes configured to support a portion of a blood vessel wall while providing a flow path to allow blood to flow past the balloon elements and perfuse the vessel.

Angioplasty has gained wide acceptance as an efficient and effective method of treating constrictions caused by undesirous tissue growth or lesions on the inner walls of blood vessels. Such tissue growth or lesions result in a narrowing ("stenosis"), which severely restricts or limits the flow of blood through the blood vessel. In the most widely used form of angioplasty, a catheter carrying a dilatation balloon is guided through the vascular system. With the aid of fluoroscopy, a physician is able to position the balloon across the stenosis. The balloon is then inflated by applying fluid pressure through an inflation lumen of the catheter to the balloon. Inflation of the balloon compresses the stenosis and opens the constriction to reestablish acceptable blood flow through the artery.

Occasionally, the need arises to temporarily support the arterial wall following dilatation of the artery. In some instances, this is occasioned by the formation of a flap in the inner artery wall. Such a flap, which is generally defined by a helical tear in the artery wall, may inhibit or restrict the flow of blood through the artery. In other instances, the need is brought about by a collapse or spasm of the artery. A variety of catheters are presently used for temporary support of the artery wall.

Prolonged occlusion of a blood vessel poses serious risk of damage to the tissue, downstream from the occlusion, which is deprived of oxygenated blood. This places a limitation on the length of time a balloon can remain expanded within an artery. Perfusing the artery while a balloon is inflated allows the balloon to remain inflated for an extended period of time. Also, since arteries may branch in the region occluded by a balloon, perfusion may provide a continuation of blood flow to the arterial side branches.

U.S. Pat. No. 4,581,017 issued Apr. 8, 1986 for CATHETER SYSTEMS in the name of Harvinder Sahota teaches a segmented or lobed dilatation balloon which forms blood flow passages between the balloon lobes. That is, the Sahota patent provides lobes positioned around the catheter body to provide a dilatation balloon while allowing blood to flow in passages formed by circumferentially adjacent balloon lobes. U.S. Pat. No. 4,983,167 issued Jan. 8, 1991 for BALLOON CATHETERS, also in the name of Harvinder Sahota, teaches, in FIG. 14, a one-sided dilatation balloon which provides a lower profile than a balloon that completely encircles the catheter body. The latter Sahota patent also discloses a multi-lobed dilatation balloon catheter.

SUMMARY OF THE INVENTION

The present invention provides a support balloon catheter which includes an elongated catheter body having a plurality of balloon elements or lobes. Each balloon lobe is configured to contact and support a body conduit wall, while providing a blood flow passage. In a preferred embodiment, the lobes form a composite support platform along a portion of the catheter body and define a flow path. In a specific preferred embodiment, the lobes extend radially from the catheter body and are positioned longitudinally along the catheter body in a desired circumferential (angular) orientation relative to each other. The relative circumferential orientation of the lobes may define a helical support structure while providing a helical flow path.

BRIEF DESCRIPTION OF THE DRAWINGS

FIG. 3 is a longitudinal sectional view of the multi-lobed support balloon of FIG. 2;

FIG. 4 is a cross-sectional view of the multi-lobed perfusion balloon of FIG. 3 taken along line 4—4;

FIG. 5 is a longitudinal sectional view of an artery with the multi-lobed perfusion balloon of FIG. 3, shown in perspective, inflated with the artery; and FIG. 6 is an elevational side view of an alternate embodiment of a multi-lobed perfusion balloon in accordance with the present invention.

DETAILED DESCRIPTION OF THE PREFERRED EMBODIMENTS

For the purposes of this specification and claims, a "support balloon catheter" is a catheter used during or following an angioplasty procedure, which is configured and used to engage (contact) and support the blood vessel. This is in contrast to a dilatation balloon catheter which is configured and used to engage a blood vessel and stretch the vessel and/or compress a stenosis toward the vessel wall. In either case, perfusion may be desirable, for reasons well known in the art.

Figure 1:
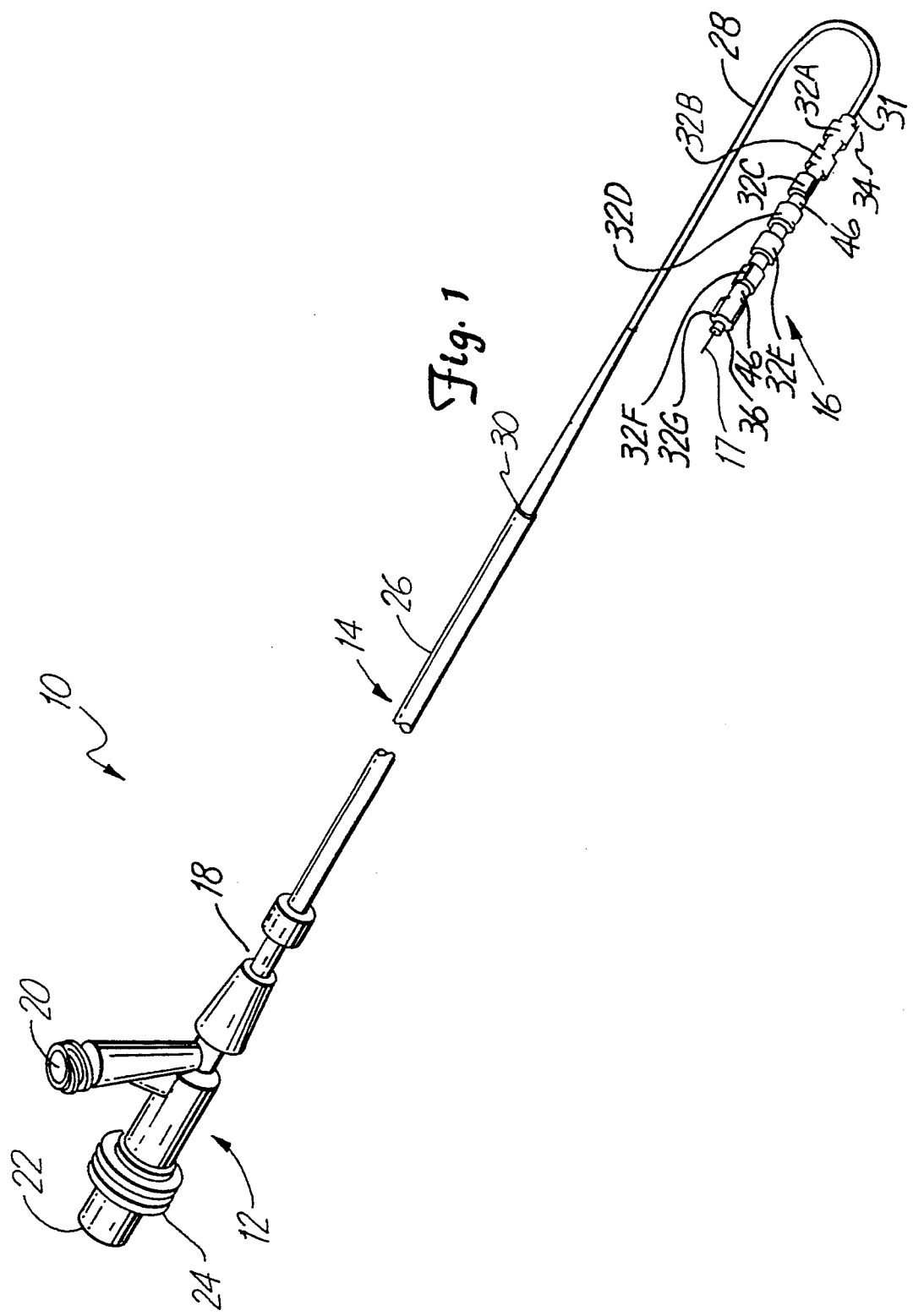
FIG. 1 is a perspective view of a perfusion support balloon catheter in accordance with the present invention.

FIG. 1 is a perspective view of support balloon catheter 10 (which generally includes manifold 12, shaft 14, and balloon head 16) and guide wire 17. Manifold 12, which is connected to shaft 14 at proximal end 18, includes inflation fluid port 20, guide wire port 22 and fitting 24. Inflation fluid port 20 is provided to receive an inflation device (not shown) which provides inflation fluid under pressure to balloon head 16. Guide wire port 22 is provided to accept guide wire 17 over which catheter 10 can be guided through a blood vessel. With the exception of balloon head 16, catheter 10 conforms to known angioplasty dilatation balloon catheters. As is known in the art, fitting 24 is provided to create a seal around guide wire 17, when it is present within manifold 12 and shaft 14, to prevent the escape of blood out of guide wire port 22.

Shaft 14 may be any of a number of shaft materials typically used for angioplasty catheters, such as polyethylene, polyimide, or stainless steel hypotubing. Shaft 14 may be comprises of a single material, a composite, or multiple individual materials. In one preferred embodiment, shaft 14 includes proximal shaft section 26 and distal shaft section 28. Proximal shaft section 26 is preferably relatively stiff to ensure good pushability of shaft 14. In another embodiment proximal shaft section 26 is a composite tube formed by a stainless steel braid which is encased in polyimide.

Distal shaft section 28 is preferably relatively flexible to permit tracking through relatively tortuous regions of the vascular system. For this purpose, distal shaft section 28 may be formed from a tube of high density polyethylene. Distal shaft section 28 may be connected by either an adhesive, such as HB Fuller 3549, or heat bonded to proximal shaft section 26 at connection region 30.

In accordance with the present invention, the balloon head 16 includes a body portion 46, which is essentially an extension of the catheter body of shaft 14, and a plurality of lobes 32A–32G which extend radially from and longitudinally along the body portion 46 for engagement and support of a vessel wall. As described more fully below, the lobes 32A–32G extend helically along the body of balloon head 16 and define a helical flow path around the balloon head 16 body portion 46. In the illustrated embodiments, each of the lobes 32A–32G define a flow passage and are positioned longitudinally along the body 46 with the flow passage of adjacent lobes being circumferentially (angularly) displaced from each other. As shown in the Figures, the lobes 32A–32G extend along the body of balloon head 16 between its proximal and distal ends 34 and 36, respectively. However, it will be apparent that balloon lobes in accordance with the present invention may be positioned in any other desired location and/or orientation along the catheter body.

Figure 2:
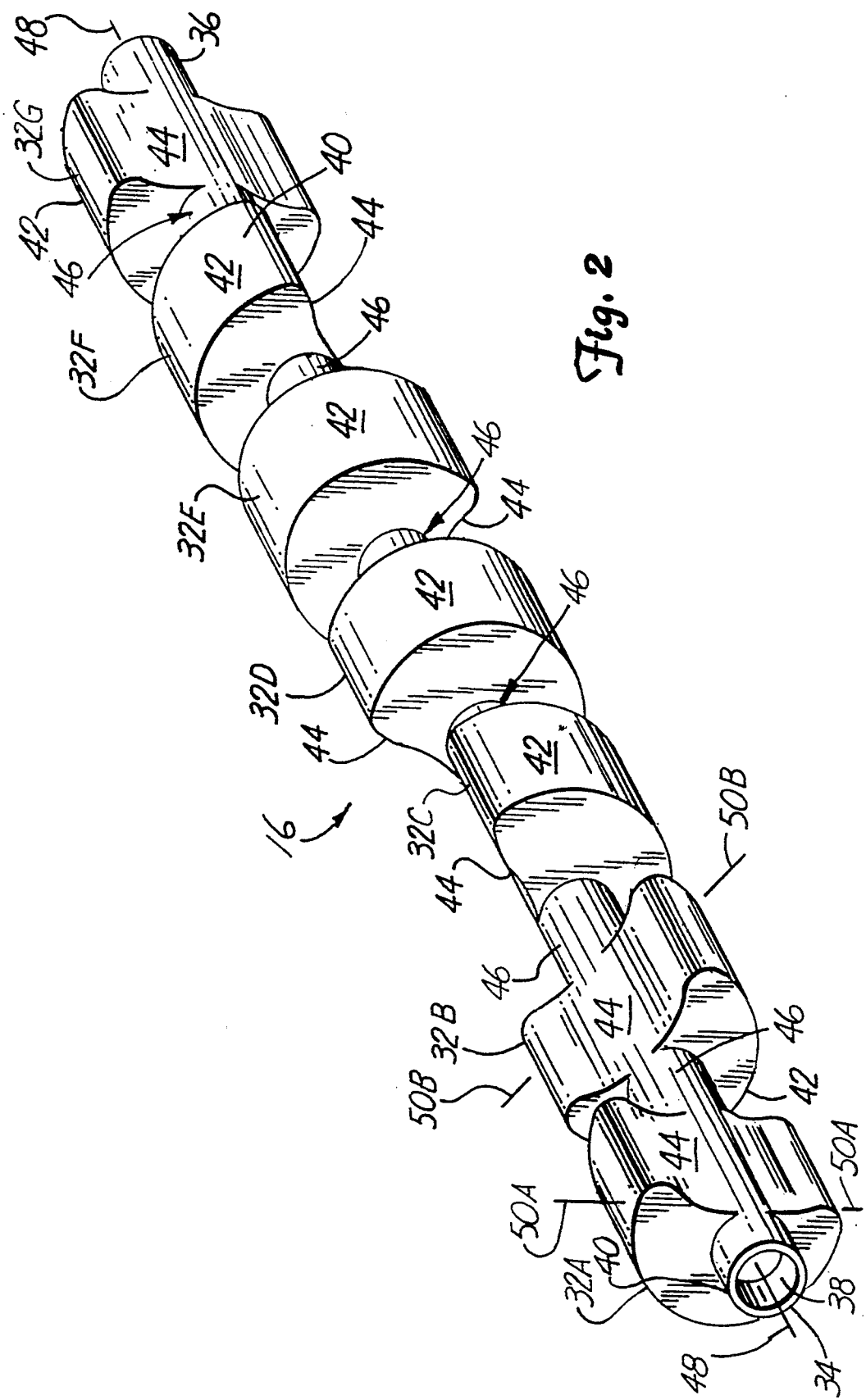
FIG. 2 is an enlarged perspective view of a portion of the support balloon catheter of FIG. 1.

FIG. 2 is an enlarged perspective view of multi-lobed balloon head 16 in an inflated state. Multi-lobed balloon head 16 includes interior surface 38, outer surface 40, and inflatable lobes 32A–32G. As shown in FIG. 2, proximal end 34 and distal end 36 are generally cylindrical, while each inflatable lobe 32 is generally partially cylindrical—the outer surface of each inflatable region 32A–32G being defined by curved vessel contact surface 42 and face 44. Each surface 42 defines an arc of less than 360 degrees and, in a preferred embodiment, defines an arc between about 90 degrees and about 70 degrees. Inflatable lobes 32A–32G are longitudinally spaced by non-inflatable regions 46 which correspond to the outer surface 40. For the sake of illustration, the length of each non-inflatable region 46 is exaggerated in FIGS. 1–5 to better illustrate the invention. A desired helical flow path 80 (see FIG. 5) along balloon head 16 is defined by the lobes and, in particular, by the faces 44 of the lobes 32. Non-inflatable regions 46, are nominally cylindrical, and have an outer diameter significantly smaller than that of contact surfaces 42 of inflatable lobes 32. Curved surfaces 42 of inflatable lobes 32 are sequentially circumferentially displaced about longitudinal axis 48 of balloon head 16 at pre-determined angular increments. In one preferred embodiment, transverse axis 50B of inflatable lobe 32B (generally along the face 44 of lobe 32B) is oriented about 60 degrees counter-clockwise from transverse axis 50A of inflatable lobe 32A (generally along the face 44 of lobe 32A). Inflatable lobes 32C–32G are similarly oriented with respect to inflatable regions 32B–32F, respectively. In particular, each lobe 32 is circumferentially displaced from adjacent lobes—by 60 degrees in the illustrated embodiment of FIG. 2. In this manner, curved surfaces 42 of inflatable regions 32A–32G define a composite spiral or helical contact surface for supporting the wall of an artery when the lobes 32 of balloon head 16 are inflated within an artery. In general, each lobe is circumferentially displaced from adjacent lobes by an angle less than the arc of its contact surface 42—creating an "overlap" in the circumferential support of the vessel. Further, the number of lobes is selected such that the sum of the circumferential displacements of all of the lobes totals at least 360 degrees.

Balloon head 16 is preferably made from a single polymer tube. One preferred material for balloon head 16 is a polyolefin copolymer, such as Surlyn from Dupont. However, other materials suitable for the construction of inflatable balloons such as polyimide and polyethylene terephthalate (PET), may be used. In addition, the balloon may be constructed in multiple layers, in known manner.

Balloon head 16 may be formed by a blow molding process. Polymer tubing is placed within a single unitary mold having a plurality of cavities corresponding to the desired arrangement of inflatable lobes 32A–32G. One end of the tubing is occluded, while the opposite end of tubing is connected to a pressure source. At least one cavity of the mold is then inserted into a water bath which has a temperature sufficient to prepare the polymer for blow molding. In a preferred embodiment, using polyolefin tubing, the hot water bath is preferably heated to a temperature of at least 81° C. A constant pressure of about 100 pounds per square inch is applied within the polyolefin tubing. With the first cavity submerged in the hot water bath, the pressure applied within the polyolefin tubing causes the tubing to expand into the first cavity and thereby form inflatable lobe 32A. The mold is then submerged to a point corresponding to the next adjacent cavity to expand the tubing into the cavity and form inflatable lobe 32B. The process of submerging the mold is repeated to form inflatable lobes 32A–32G. When all of inflatable lobes 32A–32G have been formed, the mold is quenched in a cold water bath. Multi-lobed balloon head 16 is then withdrawn from the mold and the occluded end is opened or severed.

In one preferred embodiment, multi-lobed balloon head 16 has a length of about 41 millimeters. Each inflatable lobe 32A–32G preferably has a length of about 5 millimeters, while non-inflatable regions 46 preferably have a length of about 1 millimeter. Distal end 36 and non-inflatable regions 46 of multi-lobed balloon head 16 preferably have an inner diameter of about 0.025 to about 0.027 inches and an outer diameter of about 0.032 to about 0.034 inches. Proximal end 34, due to the blow molding process, has an inner diameter of about 0.033 to about 0.035 inches and an outer diameter of about 0.040 to about 0.042 inches, which facilitates attachment of proximal end 34 of multi-lobed balloon 16 to shaft 14. When inflated, curved surface 42 of each inflatable region 32 defines a radius of about 0.750 millimeters for smaller profile balloons to about 3.00 millimeters for larger profile balloons.

FIG. 3 is a longitudinal sectional view of multi-lobed balloon head 16 with shaft 14 connected to balloon head 16. As shown in FIG. 3, shaft 14 includes inner tube 60 concentrically positioned within shaft 14 and balloon head 16, and extending to distal end 36 of balloon head 16. Inner tube 60 has a nominal outer diameter of about 0.0215 inches, which is smaller than an inner diameter of distal shaft section 28 and non-inflatable regions 46. An annular lumen 61, formed between tube 60 and shaft 14, communicates with each interior 63 of inflatable lobes 32A–32G. Outer surface 62 of inner tube 60 is connected to inner surface 38 of multi-lobed balloon 16 at distal end 36 by bond 64. Bond 64 is preferably an adhesive bond, (such as HB Fuller 3549 or Tracon) which is capable of providing a fluid tight seal. Inner tube 60 provides a guide wire conduit for guide wire 17 to allow catheter 10 to be advanced over guide wire 17 once guide wire 17 has been prepositioned within an artery.

In a preferred embodiment, distal end 28 of shaft 14 has a nominal outer diameter of about 0.0330 inches and a nominal inner diameter of about 0.0275 inches. Distal end 28 of shaft 14 is positioned within proximal end 34 of multi-lobed balloon head 16 and secured thereto by adhesive bond 66. With balloon head 16 connected to shaft 14, inflation fluid is provided to each interior 63 of inflatable lobes 32A-32G via annular lumen 61 to inflate and deflate lobes 32A-32G dependent on the fluid pressure applied.

FIG. 4 is a cross-sectional view of an inflated multi-lobed balloon head 16 in accordance with the present invention, taken along line 4—4 of FIG. 3 and positioned within an artery 70. For simplicity, only inflatable regions 32B and 32C are shown. As shown in FIG. 4, inflatable lobe 32B contacts wall 72 of artery 70 only along curved contact surface 42. A space 74B remains between artery wall 72 and face 44B of inflatable lobe 32B, which defines a flow passage and allows blood to flow past inflatable lobe 32B. In one preferred embodiment, inflatable lobe 32B has a curved support surface 42 which defines an arc of approximately 216 degrees and has an inflated cross-sectional surface area which is about 60 percent of the cross-sectional surface area of artery 70. Thus, space 74B provides a generous passage for blood flow.

As viewed in FIG. 4 (along a longitudinal axis generally defined by guide wire 17) inflatable lobe 32C is oriented approximately 60 degrees counter-clockwise from inflatable lobe 32B. That is, lobe 32C is circumferentially displaced by approximately 60 degrees from lobe 32B. In the illustrated embodiment, each of lobes 32 is circumferentially (angularly) displaced from adjacent lobes to provide a flow path along the balloon head 16. The close proximity and radial overlapping of curved contact surfaces 42 of inflatable lobes 32B and 32C ensure that a substantial portion of artery wall 72 is engaged when multi-lobed balloon head 16 is inflated within artery 70. Multi-lobed balloon 16 is therefore able to remain inflated within an artery to support the artery for an extended period of time while maintaining blood flow. Preferably, at least a 360 degree arc of artery wall 72 is supported by contact surfaces 42 from the proximal to the distal ones of lobes 32. Also, it should be noted that the surfaces 42 of lobes 32 combine to form a composite helical vessel contact surface while the spaces 74 define a helical flow path.

FIG. 5 is an enlarged perspective view of multi-lobed balloon head 16 inflated within artery 70 and adjacent to artery side branch 76. Inflation of inflatable lobes 32A-32G causes each curved surface 42 of inflatable lobes 32A-32G to expand and contact artery wall 72. The close proximity and sequential circumferential or angular displacement of each contact surface 42 of inflatable lobes 32 about the longitudinal axis of balloon head 16 permit balloon head 16 to act as a helical scaffold for artery wall 72. Multi-lobed balloon head 16 is therefore especially well suited for securing a dissection or a flap of an artery wall, or for preventing artery 70 from collapsing following a dilatation procedure. In addition, because inflatable lobes 32 are spaced in a helical array, inflated balloon head 16 is relatively flexible and capable of adapting to various artery contours 70.

As described above, the helical orientation of inflatable lobes 32 permits blood to flow through and beyond balloon head 16 when it is inflated within artery 70. As can be seen in FIG. 5, faces 44A-44G of inflatable lobes 32A-32G are spaced from artery wall 72 when inflatable lobes 32A-32G are inflated. Consequently, blood is permitted to perfuse between faces 44A-44G and artery wall 72 along helical flow path 80. Because non-inflatable regions 46 communicate with each space 74 of inflatable lobes 32A-32G, helical flow path 80 also provides for blood access to artery side branch 76, in the event multi-lobed balloon head 16 is inflated across such an artery side branch.

FIG. 6 is an enlarged elevational side view of an alternative embodiment of multi-lobed balloon head 16' in accordance with the present invention, in an inflated state. As shown in FIG. 6, each inflatable lobe 32A'-32G' of multi-lobed balloon 16' includes artery wall contact regions 42 and tapered regions 84. Tapered regions 84 form partial cones which extend longitudinally from curved contact surfaces 42 to non-inflatable regions 46. Preferably, tapered regions 84 are sloped at an angle of about 45 degrees. Tapered region 84 reduces the amount of material necessary to form inflatable lobes 32A'-32G', which improves rewrappability and reduces the distal profile of shaft 14.

The arc defined by curved contact surface 42 of each of inflatable lobes 32 can be varied. However, to define a flow passage, that arc must be less than 360 degrees. Preferably, each curved surface 42 defines an arc of between about 90 degrees and about 270 degrees. As the included angle of the arc increases, the number of inflatable lobes required to provide support around the entire circumference of the supported vessel is reduced for a given circumferential displacement. In addition, the circumferential (angular) displacement between adjacent inflatable regions 32 may be varied.

As can be appreciated, the numbers of configurations and orientation of inflatable lobes 32 may be varied according to the desired objective. While the described embodiments relate to inflatable regions which are sequentially oriented to form a composite spiral or helical contact surface, other configurations forming composite contact surfaces are contemplated by the present invention. By composite contact surfaces, it is meant that an overlap exists between adjacent contact surfaces as described above with reference to FIG. 4. By varying the arc and orientation of each contact surface 42, multi-lobed balloon head 16 is capable of accommodating a variety of arterial contours and conditions, while providing support to an arterial wall and allowing blood to flow through multi-lobed balloon head 16. Also, non-inflatable regions 46 can be omitted, so that adjacent inflatable lobes 32 abut one another. Although the present invention has been described with reference to preferred embodiments, workers skilled in the art will recognize that changes may be made in form and detail without departing from the spirit and scope of the invention.

What is claimed is:

1. In a perfusion balloon catheter of the type wherein a plurality of independent balloon lobe means extend from the catheter body for engagement of a vessel wall while allowing blood to perfuse the vessel, the improvement wherein each independent lobe means is independently formed in the catheter body by a blow molding process to extend radially from the catheter body and comprises means for supporting the vessel wall and means defining a flow passage, the lobe means being positioned, relative to each other, longitudinally along the catheter body and being circumferentially oriented independently of adjacent lobe means.

2. The perfusion balloon catheter of claim 1, wherein the flow passage of at least some adjacent lobe means are circumferentially displaced from each other.

3. The perfusion balloon catheter of claim 2, wherein the flow passage of said plurality of lobe means define a helical flow passage along said catheter body.

4. The perfusion balloon catheter of claim 1, wherein the flow passage of said plurality of lobe means define a helical flow passage along said catheter body.

5. The perfusion balloon catheter of claim 1, wherein each lobe means includes a circumferential vessel contact surface defining an arc less than 360 degrees.

6. The perfusion balloon catheter of claim 5, wherein the vessel contact surface of adjacent lobe means are circumferentially displaced from each other.

7. The perfusion balloon catheter of claim 5, wherein said vessel contact surfaces form a composite vessel contact surface.

8. The perfusion balloon catheter of claim 5, wherein said circumferential contact surfaces define an arc of between about 90 degrees and about 270 degrees.

9. The perfusion balloon catheter of claim 1, wherein said lobe means and a portion of said catheter body are unitary.

10. The perfusion balloon catheter of claim 1, wherein said lobe means form a composite vessel contact surface.

11. In a perfusion balloon catheter of the type wherein a plurality of independent balloon lobe means extend from the catheter body, the improvement wherein each independent lobe means is independently formed in the catheter body by a blow molding process to extend radially from the catheter body and comprises means for engaging a vessel wall and means defining a flow passage, the lobe means being positioned, relative to each other, longitudinally along, and circumferentially about, the catheter body independently of adjacent lobe means with the flow passage of at least some adjacent lobe means being circumferentially displaced from each other.

12. In a perfusion balloon catheter of the type wherein a plurality of balloon lobe means extend radially from the catheter body for engagement of a vessel wall while allowing blood to perfuse the vessel, the improvement wherein the lobe means include a generally partially cylindrical outer contact surface defining an arc between about 90° and 270°, the lobe means being longitudinally spaced from each other along the catheter body and being circumferentially displaced from adjacent lobes by an angle less than the arc of its outer contact surface.

* * * * *